(12) United States Patent
Herskowitz et al.

(10) Patent No.: US 8,877,153 B2
(45) Date of Patent: Nov. 4, 2014

(54) ADSORBENT FOR ULTRADEEP REMOVAL OF SULFUR COMPOUNDS FROM DISTILLATE FUELS

(75) Inventors: Mordechay Herskowitz, Beer-Sheva (IL); Miron Landau, Beer-Sheva (IL); Iehudit Reizer, Beer-Sheva (IL); Alberto Ravella, Fairfax, VA (US); James E. Kegerreis, Fairfax, VA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 21 days.

(21) Appl. No.: 13/489,607

(22) Filed: Jun. 6, 2012

(65) Prior Publication Data
US 2013/0330555 A1  Dec. 12, 2013

(51) Int. Cl.
*B01D 53/48* (2006.01)
*B01J 20/02* (2006.01)

(52) U.S. Cl.
CPC ............... *B01J 20/0259* (2013.01); *C07D 7/12* (2013.01)
USPC .................. 423/244.02; 423/244.06; 585/820; 585/823; 208/208 R; 208/244

(58) Field of Classification Search
USPC ............... 428/402–407; 95/135; 96/153, 154; 427/201; 210/660, 690; 585/820, 823; 208/208 R, 244; 423/244.01, 244.02, 423/244.06
See application file for complete search history.

(56) References Cited

U.S. PATENT DOCUMENTS

| 5,268,152 A * | 12/1993 | Delzer et al. ................. 423/210 |
| 6,428,685 B2 * | 8/2002 | Khare ....................... 208/208 R |
| 7,446,075 B1 * | 11/2008 | Kolev ........................... 502/208 |
| 8,308,848 B1 * | 11/2012 | Alptekin et al. ................. 95/136 |
| 8,524,071 B2 * | 9/2013 | Landau et al. ................. 208/244 |
| 2004/0007506 A1 | 1/2004 | Song et al. |
| 2005/0043169 A1 | 2/2005 | Jhung et al. |
| 2008/0099375 A1 * | 5/2008 | Landau et al. ................. 208/244 |

FOREIGN PATENT DOCUMENTS

| WO | 0123501 A1 | 4/2001 |
| WO | 2006011300 A1 | 5/2005 |

OTHER PUBLICATIONS

Landau et al., "Ultradeep hydrodesulfurization and adsorptive desulfurization of diesel fuel on metal-rich nickel phosphides.", Industrial and Engineering Chemistry Research, (Jun. 3, 2009) vol. 48, No. 11, pp. 5239-5249.; ISSN: 0888-5885.
Ko et al., "Surface status and size influences of nickel nanoparticles on sulfur compound adsorption", Applied Surface Science (2007), 253(13), 5864-5867; ISSN: 0169-4332.
Wang et al., "Hydrodesulfurization of dibenzothiophene over siliceous MCM-41-supported nickel phosphide catalysts.", Journal of Catalysis, (Jan. 25, 2005) vol. 229, pp. 314-321; ISSN: 0021-9517.
Sun et al., "Dibenzothiophene hydrodesulfurization activity and surface sites of silicasupported MoP, Ni2P, and Ni-Mo-P catalysts.", Journal of Catalysis, (Dec. 10, 2004) vol. 228, pp. 298-310; ISSN: 0021-9517.
Park et al., "Reactive adsorption of sulfur compounds in diesel on nickel supported on mesoporous silica", Applied Catalysis, B: Environmental (2008), 81(3-4), pp. 244-250; ISSN: 0926-3373.
Hernandes-Maldonado et al, "Desulfurization of Liquid Fuels by Adsorption via δ Complexation with Cu(I)-Y and Ag-Y Zeolites", Ind. Eng. Chem. Res. 2003, 42, pp. 123-129.
Nelson et al., "On the structure and composition of the phosphosulfide overlayer on Ni2P at hydrotreating conditions", Journal of Catalysis 241 (2006) pp. 180-188; ISSN: 0021-9517.

* cited by examiner

*Primary Examiner* — Frank Lawrence
(74) *Attorney, Agent, or Firm* — David M. Weisberg

(57) ABSTRACT

Novel adsorbents and their use in a process for the removal of sulfur compounds from distillate fuels are described herein. The novel adsorbents are comprised of nanocrystals of Ni having adsorbed on their surface phosphorus and/or phosphine species, which nanocrystals can be distributed in a micro-/meso-porous support material.

12 Claims, 7 Drawing Sheets

ADSORBENT FOR ULTRADEEP REMOVAL OF SULFUR COMPOUNDS FROM DISTILLATE FUELS

FIELD OF THE INVENTION

The present invention relates to novel adsorbents and their use in a process for the removal of sulfur compounds from distillate fuels. The novel adsorbents can comprise nanocrystals of Ni having adsorbed on their surface phosphorus species and/or phosphine species. The nanocrystals can be distributed in a micro-/meso-porous support material.

BACKGROUND OF THE INVENTION

A significant amount of research and development is being done to achieve ultra-deep desulfurization of transportation fuels, such as gasoline and distillates such as diesel and jet fuel. The sulfur content in the transportation fuels is considered an environmental concern primarily because, upon combustion, sulfur can be converted to $SO_x$, which not only contributes to acid rain, but also poisons the catalytic converter for exhaust emission treatment. Because $SO_x$ can, under certain circumstances, have harmful effects on people and the environment, the U.S. Environmental Protection Agency (EPA) classifies it as a criteria pollutant. In order to reduce the sulfur pollutant at the source, EPA regulations required reduction of the sulfur content in motor gasolines from an average of 300 wppm to 30 wppm by 2006 and in diesel fuels from 500 wppm to 15 wppm by 2006. Further reduction of sulfur from 30 wppm in motor gasolines and from 15 wppm in diesel fuels to 1 wppm or below is postulated to eventually be required for developing advanced gasoline-/diesel-based fuel cell transportation, as well as ultra-clean liquid fuel-based stationary and portable fuel cell systems.

Currently, sulfur removal from various liquid hydrocarbon streams is achieved by catalytic hydrodesulfurization (HDS) processes at temperatures ranging from about 300° C. to about 400° C. and about 3 MPa to about 6 MPa hydrogen pressure with relatively high hydrogen consumption. One criticism of conventional (catalytic) HDS technology is that, in order to reduce the sulfur content of a transportation fuel from 15 wppm to less than 1 wppm, the catalyst bed volume, or the catalyst activity, must be increased by at least about 65% compared to those values from current refinery catalysts, because the remaining sulfur compounds in the fuels, such as commercial ultra-low sulfur diesel, are the most refractory sulfur compounds (i.e., the most difficult to remove). It is well known that increases in both the reactor volume and the catalyst volume are very costly. Working at relatively high temperatures and relatively high pressures can also limit conventional HDS processes in on-site and on-board desulfurization applications, due to the complication and safety of the overall process. Furthermore, costs of supplying, purifying, and recovering hydrogen gas for such HDS processes are not negligible. Therefore, it is desired to develop other technologies for the ultra-deep desulfurization of transportation fuels.

Various relatively new approaches for ultra-deep desulfurization of liquid hydrocarbon fuels have been reported. Among them is a technology wherein sulfur species are adsorbed on nickel-based sorbents, because of their relatively high capacity and selectivity, without requiring the use of hydrogen gas. For example, U.S. Patent Application Publication No. 2008/0099375 teaches a material comprised of a mixture of nickel phosphides $Ni_2P$, $Ni_{12}P_5$, and $Ni_3P$ deposited on silica support at relatively high dispersion that can be used for ultra-deep desulfurization of diesel fuel. The sulfur content is taught as being reduced to the levels of residual sulfur of about 1 ppm and less. The ability of nickel phosphides for conversion of hydrocarbons existing in diesel fuel to carbonaceous deposits is believed to be low. Therefore, the material can be regenerated in a reducing atmosphere. But the Ni compositions and process of the '375 publication have two disadvantages. First, the single-pass sulfur capacity does not exceed 1.6 grams per 100 grams of sorbent. And second, the relatively low adsorption rate of sulfur compounds from a hydrocarbon stream by nickel phosphide phases is not best compatible with increased LHSVs (e.g., at least 5 $hr^{-1}$) during continuous desulfurization.

Therefore, there exists a need in the art for improved materials and processes for removing substantially all sulfur moieties from transportation fuels.

SUMMARY OF THE INVENTION

A first aspect of the present invention relates to an adsorbent composition for removing sulfur moieties from a hydrocarbon feed, the composition comprising: a nanocrystal complex comprised of approximately 2-10 nm sized crystals of elemental Ni having associated therewith a plurality of chemical moieties selected from the group consisting of elemental phosphorus, phosphine moieties ($PH_x$), and combinations thereof, wherein said nanocrystal complex exhibits a molar ratio of P to Ni from about 0.2 to about 0.6, and wherein said nanocrystal complex is supported on a refractory support material.

A second aspect of the present invention relates to a sulfur-adsorbed composition comprising the adsorbent composition of the first aspect of the present invention, to which at least about 1.8 grams (or at least about 2 grams) of sulfur compounds per 100 grams of adsorbent composition are adsorbed.

A third aspect of the present invention relates to a process for making an adsorbent for removing sulfur from a hydrocarbon stream, said process comprising: (a) providing a support selected from the group consisting of micro-mesoporous silica, mesoporous silica, meso-structured silica, alumina, and mixtures and combinations thereof; (b) depositing on said support a combination of nickel oxide and one or more $Ni_y$—$P_z$—$O_n$ complexes, wherein y is from 1 to 3, z is from 2 to 4, and n is from 7 to 12, and wherein the combination of nickel oxide and one or more $Ni_y$—$P_z$—$O_n$ complexes have a first average particle size; and (c) reducing said combination of nickel oxide and $Ni_y$—$P_z$—$O_n$ complexes, thereby resulting in a plurality of Ni nanoparticles having a second average particle size and with which is (are) associated one or more chemical species selected from the group consisting of elemental phosphorus, phosphine ($PH_x$) species, and combinations thereof, wherein: (i) the second average particle size is smaller than the first average particle size by up to 80%, by at least 15%, or both; (ii) the first average particle size is in the range from about 4 nm to about 10 nm and the second average particle size is in the range from about 2 nm to about 6 nm; or (iii) both (i) and (ii).

A fourth aspect of the invention relates to a method for adsorptive removal of sulfur from a hydrocarbon stream comprising: (i) contacting said hydrocarbon stream with the adsorbent composition of the first aspect of the invention under conditions sufficient to achieve a single-pass adsorption capacity for sulfur compounds of more than 1.6 grams of sulfur compounds per 100 grams of adsorbent composition, wherein the refractory support comprises silica, silica-alumina, carbon, or a combination thereof; (ii) contacting said hydrocarbon stream with an adsorbent composition comprising a nanocrystal complex including nanocrystals of elemental Ni having associated therewith a plurality of chemical moieties selected from the group consisting of elemental phosphorus, phosphine moieties ($PH_x$), and combinations thereof, wherein said nanocrystal complex exhibits a molar ratio of P to Ni from about 0.2 to about 0.6, and wherein said nanocrystal complex is supported on a refractory support material comprising silica, silica-alumina, carbon, or a combination thereof, so as to achieve the sulfur-adsorbed composition of the second aspect of the invention; or (iii) contacting said hydrocarbon stream with an adsorbent composition made according to the process of the third aspect of the invention, wherein the refractory support comprises silica, silica-alumina, carbon, or a combination thereof. In this aspect, in order for the method to be adsorptive, instead of mostly catalytic, the sulfur removal method can advantageously be accomplished without added hydrogen.

DETAILED DESCRIPTION OF THE EMBODIMENTS

Figure 1:
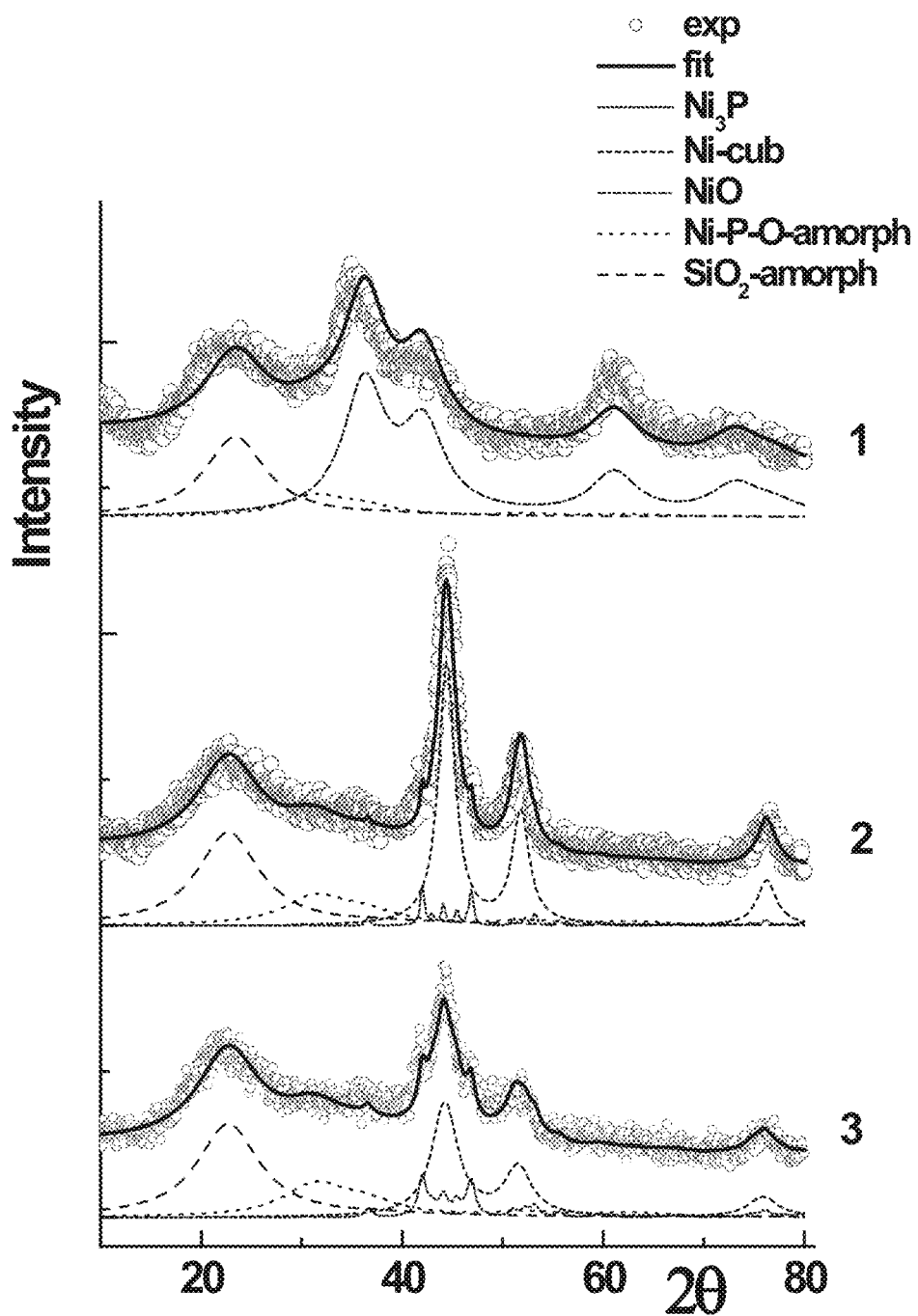
FIG. 1 shows XRD patterns of fresh, reduced, and used Ni–P/$SiO_2$ adsorbent.

The present invention was originated from an observation that, at relatively low phosphorus contents (corresponding to an Ni/P ratio from ~4.5 to ~8.5) in the starting oxide form of an Ni—P material, thermo-programmed reduction (TPR) does not generally produce pure nickel phosphide phases. A combination of nickel oxide (NiO) and nickel phosphate ($Ni_2P_2O_7$) phases/complexes in the material can be converted, after TPR, to relatively small nanocrystals (e.g., about 4-10 nm or about 4-6 nm) of a metallic nickel ($Ni^\circ$) phase, to which can be adsorbed elemental phosphorus and/or phosphine ($PH_x$) species. The metallic nickel phase can adsorb sulfur compounds (e.g., from a hydrocarbon stream) at a relatively high rate. The adsorbed species, notably, can tend to inhibit other reactions involving (e.g., conversion of hydrocarbons, such as in a diesel fuel, to carbonaceous species that can typically deposit on) the metallic nickel phase. This can result in increasing the life of the adsorbent. Additionally or alternately, phosphorus species adsorbed on the $Ni^\circ$ nanoparticles/phases can be important, e.g., as their propensity to react with the Ni nanoparticles under adsorptive (different from catalytic) desulfurization conditions (for instance, from ~150° C. to ~400° C., typically with substantially no added hydrogen), which can in turn result in a desirable formation of only partially phosphided nickel nanoparticles (e.g., advantageously including a $Ni_3P$ phosphide phase). This can be a relatively slow process that can enhance the sulfur sorption capacity of the adsorbent, e.g., according to a dual mechanism. A $Ni^\circ$ surface can be generated for relatively fast adsorption of sulfur compounds, which can be accompanied by a decrease in the $Ni^\circ$ crystal size, e.g., from about 4-10 nm to about 2-6 nm and/or representing at least a 15% reduction (such as at least a 20% reduction, at least a 25% reduction, at least a 30% reduction, at least a 35% reduction, at least a 40% reduction, at least a 45% reduction, or at least a 50% reduction) and/or representing up to an 80% reduction (such as up to a 75% reduction, up to a 70% reduction, up to a 65% reduction, up to a 60% reduction, up to a 55% reduction, up to a 50% reduction, up to a 45% reduction, up to a 40% reduction, up to a 35% reduction, or up to a 30% reduction). At the same time, highly dispersed nanoparticles can be produced, advantageously including at least some of $Ni_3P$ stoichiometry, which is believed to have the highest sulfur sorption capacity among $Ni_xP$ phases (the subscript "x" in $Ni_xP$ herein is not necessarily the same as the subscript in $PH_x$ or $SO_x$ or $NO_x$, etc., but is typically used by those of ordinary skill in the art, and also herein, as a generic placeholder representing an uncertain range of discrete stoichiometric values).

Additionally or alternately, Ni particles can comprise from about 35 wt % to about 50 wt % of the active phases. The sulfur sorptive properties of these materials can advantageously be sufficient for ultra-deep desulfurization (in this case, adsorptive not catalytic), preferably in continuous or semi-continuous mode, e.g., capable of achieving about 1 wppm or less residual sulfur in diesel fuels containing at least about 10 wppm (such as at least about 15 wppm, at least about 20 wppm, at least about 25 wppm, at least about 30 wppm, at least about 40 wppm, or at least about 50 wppm; additionally or alternately not exceeding about 100 wppm, such as not exceeding about 75 wppm, not exceeding about 50 wppm, not exceeding about 40 wppm, not exceeding about 30 wppm, not exceeding about 25 wppm, not exceeding about 20 wppm, or not exceeding about 15 wppm) sulfur content, typically at LHSVs of at least 0.1 $hr^{-1}$ (e.g., at least 0.2 $hr^{-1}$, at least 0.3 $hr^{-1}$, at least 0.5 $hr^{-1}$, at least 1 $hr^{-1}$, at least 2 $hr^{-1}$, at least 3 $hr^{-1}$, at least 5 $hr^{-1}$, at least 10 $hr^{-1}$, at least 15 $hr^{-1}$, or at least 20 $hr^{-1}$) and/or of up to 100 $hr^{-1}$ (e.g., up to 75 $hr^{-1}$, up to 50 $hr^{-1}$, up to 40 $hr^{-1}$, up to 30 $hr^{-1}$, up to 25 $hr^{-1}$, up to 20 $hr^{-1}$, up to 15 $hr^{-1}$, up to 10 $hr^{-1}$, up to 8 $hr^{-1}$, up to 6 $hr^{-1}$, or up to 5 $hr^{-1}$), optionally but preferably with attendant sulfur sorption capacity exceeding 1.6 grams per 100 grams of adsorbent composition/material (e.g., at least about 1.8 grams per 100 grams, at least about 2 grams per 100 grams, at least about 2.5 grams per 100 grams, at least about 3 grams per 100 grams, at least about 3.5 grams per 100 grams, at least about 4 grams per 100 grams, or at least about 5 grams per 100 grams). Additionally or alternately, the sulfur sorptive properties of this material can be sufficient for ultra-deep desulfurization (in this case, adsorptive not catalytic), preferably in continuous or semi-continuous mode, e.g., capable of achieving at least about 80 wt % (such as at least about 85 wt %, at least about 90 wt %, at least about 92 wt %, at least about 94 wt %, at least about 95 wt %, at least about 96 wt %, at least about 97 wt %, or at least about 98 wt %; additionally or alternately up to about 99 wt %, such as up to about 98 wt %, up to about 97 wt %, up to about 96 wt %, or up to about 95 wt %) reduction in sulfur content of the hydrocarbon streams (such as diesel fuels) with which they are contacted.

The ultra-deep (adsorptive) desulfurization capability of such adsorbents can advantageously be applied to sulfur-containing hydrocarbon streams, such as fuel streams. Non-liming examples of sulfur-containing hydrocarbon streams can include, e.g., transportation fuel streams in the distillate boiling range (such as diesel fuels; jet fuels; light, intermediate, and/or heavy cycle oils; and the like; as well as combinations thereof), though a wider hydrocarbon feed applicability can also exist for naphthas, kerosene, gasoils (atmospheric and/or vacuum), highly aromatic hydrocarbons, lubricants, white oils, adhesives, waxes, and the like, and combinations thereof.

The adsorbent materials of the present invention can generally be prepared by placing an effective amount (e.g., in a lab-scale synthesis, from about 8-12 grams) of the selected support material, after calcination (typically in air, also generally at temperatures from about 500° C. to about 580° C.), into a vessel (e.g., in a lab-scale synthesis, in a ~150-500 ml flask) with the capability of being heated and/or stirred (e.g., in a heating bath, and provided with a magnetic stirrer and condenser). The vessel can advantageously also contain an effective amount of a nickel salt (e.g., prepared by aqueous dissolution), an effective amount of a strong acid (e.g., having a pKa value less than minus one), an effective amount of an oxidized phosphorus moiety (e.g., of a phosphate, such as an ammonium phosphate, perhaps selected from $(NH_4)H_2PO_4$, $(NH_4)_2HPO_4$, $(NH_4)_3PO_4$, and combinations thereof), and an effective amount of a hydrolyzing agent (such as urea). Non-limiting examples of suitable nickel salt counterions can include, but are not limited to, nitrate, acetate, formate, carbonate, bicarbonate, sulfate, hydrogen sulfate, bromide, chloride, iodide, and the like, and combinations thereof. A preferred acid can include nitric acid, specifically when the nickel salt also includes nickel nitrate.

In an exemplary lab-scale formulation, about 8-12 grams of a silica-containing support can be placed into a vessel with a mixture of about 30-150 grams of $Ni(NO_3)_2.6H_2O$, about 27-136 grams urea, about 2-11 ml of $HNO_3$ (70%), about 3.5-19 grams $(NH_4)_2HPO_4$, and about 50-240 ml of $H_2O$. The mixture can then be heated to a temperature of about 75-85° C. and stirred at this temperature for about 23-27 hours. During this period, the pH can be increased stepwise, e.g., from 0.8 to 1.1 to 4.5 to 5.5. The mixture can then be cooled to approximately room temperature (about 20-25° C.) and filtered. The resulting solid can then be washed, which, in this lab-scale formulation, can mean transferring the solid into a flask containing about 100-300 mL distilled water at ~58-62° C., stirring quickly (e.g., for ~1-2 minutes), and then filtering again (typical lab-scale experiments can include washing at least twice). The washed material can then be dried, e.g., at a temperature from about 110-130° C. for about 3-5 hours (such as at a heating rate of about 5-7° C./min), and then calcined, e.g., in air at about 480-530° C. for about 5-7 hours (such as at a heating rate of about 1-2° C./min).

Nickel Phosphate—Oxide Precursor

In an embodiment of the present invention, a combination of nickel oxide (NiO) and nickel phosphate oxide precursor $Ni_y$—$P_z$—$O_n$ (where y can be from 1 to 3, z can be from 2 to 4, and z can be from 7 to 12) can be deposited (e.g., by precipitation of the product of the interaction of corresponding salts) on the surface of a porous refractory support (e.g., silica gel), at conditions that can advantageously exclude concurrent deposition of the (individual, e.g., unsupported) nickel oxide and the (individual, e.g., unsupported) $Ni_y$—$P_z$—$O_n$ complex. The deposition (precipitation) can be conducted by a pH- and rate-controlled (urea hydrolysis) basification of a suspension of a porous refractory support material in an (acidic) aqueous solution of nickel and oxidized phosphorus salts (and urea) taken at relative amounts that can yield a composite material having an advantageous Ni/P atomic ratio (e.g., about 4.5-8.5 or about 5.0-7.0). Additionally or alternately, the nickel content in the phosphate oxide precursor can be greater than 15 wt %, e.g., at least about 20 wt %, at least about 25 wt %, at least about 30 wt %, at least about 35 wt %, from greater than 15 wt % to about 50 wt %, from about 20 wt % to about 50 wt %, from about 25 wt % to about 50 wt %, from about 30 wt % to about 50 wt %, from about 35 wt % to about 50 wt %, from greater than 15 wt % to about 45 wt %, from about 20 wt % to about 45 wt %, from about 25 wt % to about 45 wt %, from about 30 wt % to about 45 wt %, from about 35 wt % to about 45 wt %, from greater than 15 wt % to about 40 wt %, from about 20 wt % to about 40 wt %, from about 25 wt % to about 40 wt %, from about 30 wt % to about 40 wt %, from about 35 wt % to about 40 wt %, from greater than 15 wt % to about 35 wt %, from about 20 wt % to about 35 wt %, from about 25 wt % to about 35 wt %, or from about 30 wt % to about 35 wt %. In many embodiments according to the invention, the surface area of the supporting material (e.g., as measured by BET methods) can advantageously be in range of about 150 m$^2$/g to about 1000 m$^2$/g, e.g., from about 150 m$^2$/g to about 750 m$^2$/g, from about 150 m$^2$/g to about 500 m$^2$/g, from about 200 m$^2$/g to about 1000 m$^2$/g, from about 200 m$^2$/g to about 750 m$^2$/g, or from about 200 m$^2$/g to about 500 m$^2$/g. Additionally or alternately, the supporting material can have an average pore diameter from about 3 nm to about 30 nm.

The above listed chemical composition of precursor material, after final calcination (e.g., in air at about 500° C.), can typically determine the composition and state of elements in the adsorbent after TPR, advantageously yielding a relatively high sulfur sorption rate and a relatively high sulfur sorption capacity exceeding 1.6 grams sulfur content per 100 grams adsorbent material (e.g., of at least about 1.8 grams per 100 grams, of at least about 2 grams per 100 grams, of at least about 2.5 grams per 100 grams, of at least about 3 grams per 100 grams, of at least about 3.5 grams per 100 grams, of at least about 4 grams per 100 grams, or of at least about 5 grams per 100 grams). The X-ray diffraction (XRD) pattern (arbitrary intensity vs. 2θ angle) of calcined Ni—P—O/SiO$_2$ precursor, containing ~42 wt % Ni and ~3.5 wt % P (atomic Ni/P ratio ~6.3) is shown in FIG. 1 (curve 1). Aside from reflections believed to correspond with a NiO phase at 2θ peaks at ~37.3°, ~43.3°, ~62.9°, and ~75.4° (e.g., appearing to exhibit an average crystal domain size of ~2 nm, calculated by analyzing XRD peak widths) and reflections believed to correspond with an amorphous silica support phase (wide halo centered at a 2θ value of ~22°), the material can typically also contain a wide amorphous halo (at 2θ values extending from ~27° to ~40°), which is believed to correspond with a $Ni_y$—$P_z$—$O_n$ complex-phosphate phase.

The reductive treatment of the calcined sorbent precursor (e.g., in hydrogen flow at elevated temperatures such as from about 550° C. to about 650° C.) can serve to convert much, if not all, of the nickel in the NiO phase(s), and at least a portion of nickel in the $Ni_y$—$P_z$—$O_n$ complex-phosphate phase(s), substantially to metallic nickel phases, the particles embodying which phases can advantageously: (a) have an average crystal size from about 2 nm to about 6 nm, e.g., from about 3 nm to about 6 nm, or from about 4 nm to about 6 nm; (b) reduce in average crystal size, as compared to the crystal size of the deposited/precipitated phases prior to reduction, of at least 15% (e.g., of at least about 20%, of at least about 25%, of at least about 30%, of at least about 35%, of at least about 40%, of at least about 45%, or of at least about 50%); and/or (c) reduce in average crystal size, as compared to the crystal size of the deposited/precipitated phases prior to reduction, of up to about 80% (e.g., of up to about 75%, of up to about 70% about, of up to about 65%, of up to about 60%, of up to about 55%, of up to about 50%, of up to about 45%, of up to about 40%, of up to about 35% about, or of up to about 30%).

Attendant with the reduction of nickel, it is believed that at least a portion of the phosphorus in the $Ni_y$—$P_z$—$O_n$ complex-phosphate phase can also be converted during the reductive treatment, e.g., to phosphine ($PH_3$), to some form of $PH_x$, and/or to elemental phosphorus. While some of these reduced phosphorus moieties can remain adsorbed at the surface of the reduced (metallic Ni nano-) particles, at least a portion of them can be partially removed (desorbed), e.g., through the flowing action of effluent gases, thus serving to increase the atomic Ni/P ratio in such particles/phases, e.g., by about 0.5 to about 1. Such an effected can be seen experimentally, e.g., in a reduction in the intensity of wide (amorphous) halo in the XRD spectra between about 27° and 40° 2θ, in elimination of reflections at 2θ values of ~37.3°, ~43.3°, ~62.9°, and ~75.4° (believed to be characteristic of a NiO phase), and in appearance of peaks at 2θ values of ~44.5°, ~51.8°, and ~76.4° (believed to be characteristic of a substantially metallic Ni phase). For example, this can be seen in a reduced sample illustrated in FIG. 1 (curve 2), where XRD peak width was used to calculate the average crystal size of the phases as being ~5 nm. One notable distinction between the compositions and methods of the present invention (e.g., compared to prior art such as U.S. Patent Application Publication No. 2008/0099375) can be that, at the selected total Ni/P ratios in the oxide precursor, the nickel phosphide phases (e.g., $Ni_2P$, $Ni_{12}P_5$, and $Ni_3P$) were not substantially differentia table from the baseline during reductive treatment of the oxide precursor. That is, the integral intensities of reflections corresponding to $Ni_{12}P_5$ and $Ni_3P$ phosphide phases in reduced adsorbent (curve 2) appeared to be negligible (corresponding to <1 wt % total content of the selected nickel phosphides).

Figure 2:
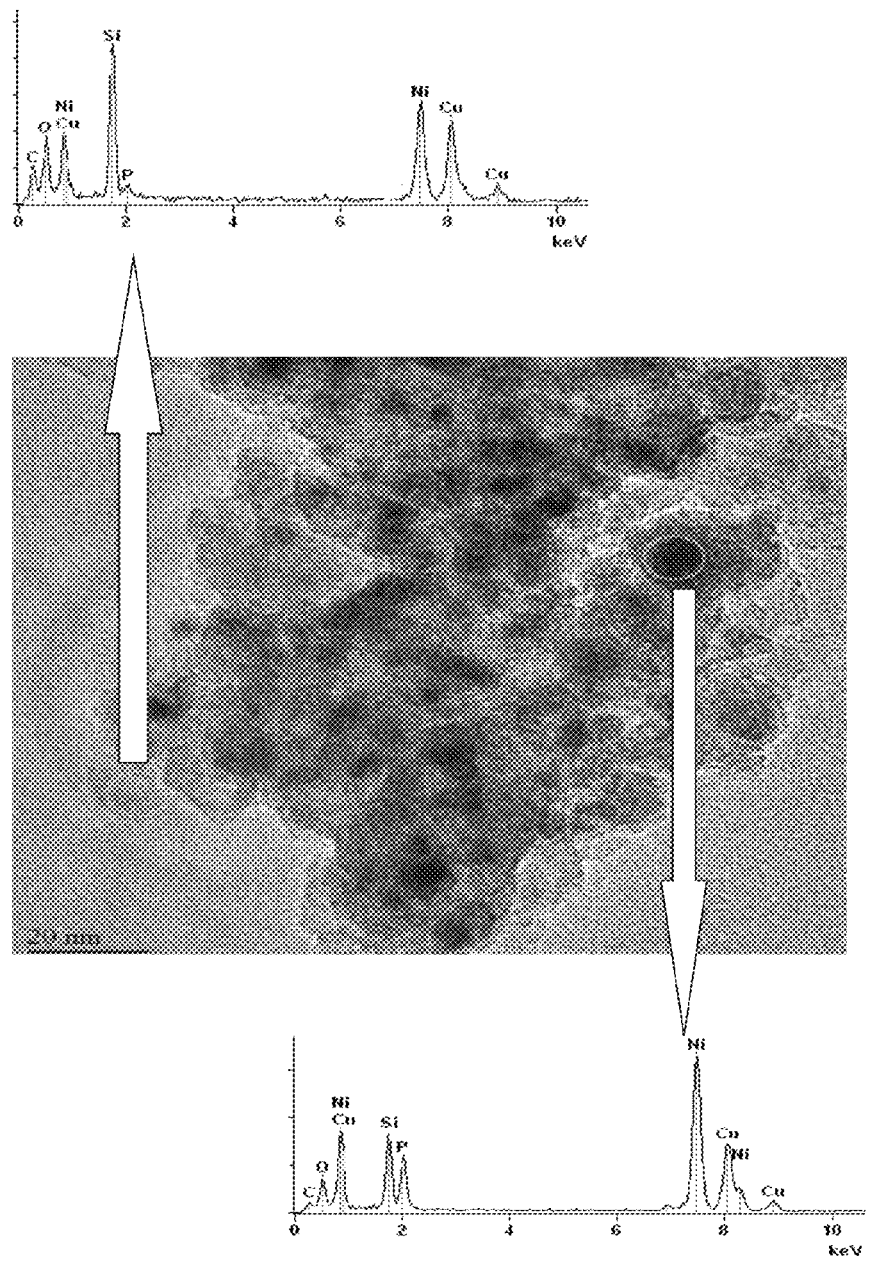
FIG. 2 shows a high-resolution TEM (HRTEM) image of a reduced adsorbent, as well as elemental analyses (EDX/EDS spectra) of certain image regions.

Without wishing to be bound by theory, it is believed that phosphorus can be located (trapped) at the surface of metallic particles of Ni—this is illustrated in FIG. 2 by the local EDX (Energy Dispersive X-ray) spectra taken (with an electronic spot diameter of ~10 nm) from the areas believed to encompass the nanoparticles, compared to the areas believed to be substantially free of the nanoparticles, based on high resolution TEM (Transmission Electron Mircroscopy) images. The integral intensity of the peaks characteristic of phosphorus was several times higher at the areas believed to be encompassed by the nanoparticles, relative to the areas believed to encompass the (silica) support and/or the areas believed to encompass unreduced $Ni_y$—$P_z$—$O_n$ complex-phosphate phases. This has been postulated herein to indicate a redistribution of Ni and P in the calcined oxide precursor during reductive treatment between nanoparticles of Ni, their surface (for phosphorus species), and residual $Ni_y$—$P_z$—$O_n$ complex-phosphate phase, which apparently resulted in a substantial enrichment of nanoparticles with phosphorus, relative to the total adsorbent composition. The change in atomic P/Ni ratio measured by local EDX analysis (see FIG. 2) of the nanoparticle areas was in the range of ~0.2 to ~0.6, while the change in P/Ni ratio of the overall adsorbent composition, according to EDX analysis (this time, with an electronic spot diameter of ~1 μm) ranged from ~0.12 to ~0.25 (with a range of atomic Ni/P extending from about 4.0 to about 8.0).

In one embodiment, the phosphorus adsorbed on the surface of the nanoparticles in the reduced adsorbent composition displayed binding energies, according to XPS (X-ray Photoelectron Spectroscopy) analysis, of its electrons at 2 p 3/2 core 127-129 eV, which are believed to correspond to elemental phosphorus and adsorbed $PH_x$ species. While not wishing to be bound to a particular theoretical structure model, it is believed that the observed phosphorus was closely associated with the nanoparticles (e.g., adsorbed on their surface, or absorbed in their several surface atomic layers). This state of the nanoparticles being closely associated with phosphorus species is further believed to effect an increased the rate of chemical reaction between sulfur-containing compounds in the hydrocarbon feed and the active sites on the nanoparticles. Again, without being bound by theory, it is believed that the phosphorus species can protect the active sites on the nanoparticles, e.g., by slowing down their deactivation vis-à-vis carbonaceous deposits. Additionally or alternately, the phosphorus species can slowly react with metallic nickel phases during (adsorptive) desulfurization, e.g., by forming a nickel phosphide phase having relatively higher sulfur sorption capacity.

In many embodiments, the adsorbent composition can advantageously have a relatively high loading of the disperse Ni phase, e.g., ranging from about 30 wt % to about 50 wt %, from about 35 wt % to about 50 wt %, from about 30 wt % to about 45 wt %, or from about 35 wt % to about 45 wt %. Additionally or alternately, the disperse Ni phase can advantageously exhibit a crystal size (average) of about 2 nm to about 6 nm, e.g., about 2 nm to about 5 nm, about 2 nm to about 4 nm, about 3 nm to about 6 nm, about 3 nm to about 5 nm, about 4 nm to about 6 nm, or about 4 nm to about 5 nm. Further additionally or alternately, the disperse Ni phase can have phosphorus and/or phosphine ($PH_x$) species associated therewith, particularly involving P/Ni atomic ratios ranging from about 0.2 to about 0.6, e.g., from about 0.2 to about 0.5, from about 0.2 to about 0.55, from about 0.25 to about 0.6, from about 0.25 to about 0.55, from about 0.25 to about 0.5, from about 0.3 to about 0.6, from about 0.3 to about 0.55, from about 0.3 to about 0.5, from about 0.35 to about 0.6, from about 0.35 to about 0.55, or from about 0.35 to about 0.5.

As mentioned above, the adsorbent composition typically includes a refractory support material. Non-limiting examples of refractory support materials that can be used in the practice of the present invention can include, but are not limited to, micro-mesoporous silica, mesoporous silica, meso-structured silica, mesoporous alumina, mesoporous silica-alumina, silica, silica-alumina, alumina, carbon, and mixtures thereof. In certain embodiments, it can be preferred that the support material have a surface area ranging from about 150 $m^2/g$ to 1000 $m^2/g$, such as from about 200 $m^2/g$ to 1000 $m^2/g$, and/or an average pore diameter ranging from about 3 nm to 30 nm. In a preferred embodiment, the adsorbent material can be prepared by reduction of nickel phosphate and nickel oxide deposited on the support from an acidified aqueous solution of a nickel salt, such as nickel nitrate, together with an ammonium phosphate salt, whether monoammonium dihydrogen phosphate, diammonium monohydrogen phosphate, or triammonium phosphate (but particularly including or being diammonium monohydrogen phosphate).

The above mentioned embodiments should not be interpreted as necessarily limiting, and it is conceived that there may be other valid techniques, apparent to those skilled in the art, for depositing the Ni nanoparticles closely associated with phosphorus/phosphine species on an inert support.

In an exemplary embodiment, a process for making an adsorbent composition useful for removing sulfur from a hydrocarbon stream can comprise the steps of: (a) providing a support (e.g., as described herein, particularly including mesoporous supports), which can, in some embodiments, exhibit surface areas and/or average pore sizes as described herein; (b) depositing on said support a combination of nickel oxide and one or more $Ni_y$—$P_z$—$O_n$ complexes (where y can be from 1 to 3, z can be from 2 to 4, and n can be from 7 to 12) having a first average particle size (and/or a first particle size range); and (c) reducing said combination of nickel oxide and $Ni_y$—$P_z$—$O_n$ complexes, thereby resulting in a plurality of Ni nanoparticles having a second average particle size (and/or a second particle size range) and with which is (are) associated one or more elemental phosphorus and/or phosphine ($PH_x$) species. In such an exemplary embodiment, one or both of the following can be satisfied: (a) the second average particle size can advantageously be smaller than the first average particle size (i) by up to 80% and/or (ii) by at least 15%; and/or (b)(i) the first average particle size (and/or the first particle size range) can be from about 4 nm to about 10 nm and/or (ii) the second average particle size (and/or the second average particle size range) can be from about 2 nm to about 6 nm. Additionally or alternately in such embodiments, the combination of nickel oxide and $Ni_y$—$P_z$—$O_n$ complex(es) can be deposited on said support so as to achieve (i) an atomic Ni/P ratio from about 4.5 to about 8.5, and/or (ii) a nickel content from about 15 wt % to about 50 wt %, based on the weight of the adsorbent composition.

The processes described herein for making an adsorbent composition that can be useful for removing sulfur from a hydrocarbon stream can advantageously result in an adsorbent material/composition that has an adsorption capacity for sulfur compounds (e.g., from the hydrocarbon feed) of more than 1.6 grams of sulfur compounds per 100 grams of adsorbent composition (e.g., of at least about 1.8 grams per 100 grams, of at least about 2 grams per 100 grams, of at least about 2.5 grams per 100 grams, of at least about 3 grams per 100 grams, of at least about 3.5 grams per 100 grams, of at least about 4 grams per 100 grams, or of at least about 5 grams per 100 grams).

Sulfur Removal Methods

Methods for adsorptive removal of sulfur from a hydrocarbon stream can advantageously involve an adsorbent material/composition (i) according to the invention and/or as described herein, (ii) made according to a manufacturing process of the invention and/or as described herein, and/or (iii) comprising a nanocrystal complex including nanocrystals of elemental Ni having associated therewith a plurality of elemental phosphorus and/or phosphine moieties ($PH_x$), said nanocrystal complex exhibiting a molar ratio of P to Ni from about 0.2 to about 0.6 and supported on a refractory support material (such as mentioned herein, e.g., comprising silica, silica-alumina, carbon, or a combination thereof).

Advantageously, such adsorptive removal methods can include contacting the hydrocarbon feed stream with the aforementioned adsorbent material/composition under conditions sufficient to achieve a single-pass adsorption capacity for sulfur compounds of more than 1.6 grams of sulfur compounds per 100 grams of adsorbent composition (e.g., of at least about 1.8 grams per 100 grams, of at least about 2 grams per 100 grams, of at least about 2.5 grams per 100 grams, of at least about 3 grams per 100 grams, of at least about 3.5 grams per 100 grams, of at least about 4 grams per 100 grams, or of at least about 5 grams per 100 grams). Additionally or alternately, regardless of the sulfur sorption capacity of the adsorbent, the adsorptive removal methods according to the invention can advantageously include contacting the hydrocarbon feed stream with the aforementioned adsorbent material/composition under conditions sufficient to form a sulfur-adsorbed material/composition according to the invention (e.g., an at least partially spent, or completely spent, adsorbent material/composition). A sulfur-adsorbed material/composition according to the invention is an adsorbent material/composition ((i) according to the invention and/or as described herein, (ii) made according to a manufacturing process of the invention and/or as described herein, and/or (iii) comprising a nanocrystal complex including nanocrystals of elemental Ni having associated therewith a plurality of elemental phosphorus and/or phosphine moieties ($PH_x$), said nanocrystal complex exhibiting a molar ratio of P to Ni from about 0.2 to about 0.6 and supported on a refractory support material) with which is closely associated (adsorbed, trapped) more than 1.6 grams of sulfur compounds per 100 grams of adsorbent composition (e.g., at least about 1.8 grams per 100 grams, at least about 2 grams per 100 grams, at least about 2.5 grams per 100 grams, at least about 3 grams per 100 grams, at least about 3.5 grams per 100 grams, at least about 4 grams per 100 grams, or at least about 5 grams per 100 grams).

In certain embodiments, the adsorptive methods according to the invention for removing sulfur compounds from a hydrocarbon feed (e.g., a liquid hydrocarbon stream, such as a distillate boiling range fuel feed) can be conducted in batch, semi-continuous, or continuous mode and can comprise: i) providing a composite adsorbent material containing one or more nanocrystalline Ni-containing phases (e.g., having an average crystal size and/or a crystal size range from about 3 nm to about 6 nm, exhibiting a nickel loading from about 30 wt % to about 50 wt %, exhibiting a nickel loading from about 35 wt % to about 45 wt %, exhibiting an Ni/P atomic ratio from about 4.0 to about 8.5, exhibiting an Ni/P atomic ratio from about 4.5 to about 8.5, and/or exhibiting an Ni/P atomic ratio from about 5 to about 7) with which is(are) associated phosphorus and/or phosphine $PH_x$, which phases are disposed on a stabilized support matrix (e.g., comprising a mesoporous silica and/or alumina, comprising a micro-mesoporous silica and/or alumina, having surface area from about 200 $m_2/g$ to about 1000 $m_2/g$, and/or having an average pore diameter from about 3 nm to about 30 nm); and ii) contacting the hydrocarbon feed with the adsorbent composite at a temperature from about 150° C. to about 400° C. (e.g., from about 250° C. to about 400° C., from about 250° C. to about 350° C., or from about 275° C. to about 360° C.). Because the sulfur removal processes according to the invention are desired to be adsorptive (not necessarily catalytic) for sulfur compounds, in many embodiments, the methods can be carried out in the substantial absence of added hydrogen. When the adsorptive sulfur removal methods are continuous or semi-continuous, the liquid hourly space velocity (LHSV) can typically be chosen to reach a required level of residual sulfur in the feed (e.g., to meet a specification and/or to meet a target sulfur content in the product effluent). In certain embodiments, therefore, the LHSV can range from about 5 $hr^{-1}$ to about 40 $hr^{-1}$, e.g., from about 8 $hr^{-1}$ to about 40 $hr^{-1}$, from about 10 $hr^{-1}$ to about 30 $hr^{-1}$, or from about 10 $hr^{-1}$ to about 25 $hr^{-1}$.

In certain embodiments, the precursor composite material of the composition and support/matric texture can yield, after reduction, an adsorbent composite material with nanoparticles containing Ni and P having an average crystal size and/or a crystal size range from about 3 nm to about 6 nm, with which nanoparticles is/are closely associated phosphorus moieties, e.g., that can serve to enhance interaction with sulfur-containing (particularly organo-sulfur) compounds, such as those typically present in petroleum-based distillate fuel streams. Without being bound by theory, the adsorbent composite is believed to have enhanced sulfur sorption capacity/capability, at least in part due to the ability of phosphorus species adsorbed on the Ni° nanoparticles (e.g., in the form of nickel phosphide phases comprising $Ni_2P$, $Ni_{12}P_5$, and/or $Ni_3P$) to associate/interact/react with (become trapped by) the sulfur moieties on the sulfur-containing compounds in the hydrocarbon feed at adsorptive desulfurization conditions (150° C. to 400° C., with no added hydrogen). As an example of this phenomenon, in one embodiment, XRD analysis of the sulfur-adsorbed composite showed 2θ peaks at ~36.4°, ~41.8°, ~43.6°, and ~46.6° (believed to be characteristic of a $Ni_3P$-containing phase that may have been formed preceding and/or during adsorptive desulfurization), as illustrated in FIG. 1 (curve 3). The formation of $Ni_3P$ nanoparticles can be a relatively slow process that is believed to enhance the sulfur capacity of the adsorbent according to the dual mechanism: potentially generating a Ni° surface for relatively fast adsorption of sulfur compounds and/or decreasing the Ni° crystal size; and/or potentially producing relatively highly dispersed $Ni_3P$-containing nanoparticles, which are currently observed to have the highest sulfur adsorption capacity among $Ni_xP$ phases. Such interaction of adsorbent phase(s) and organo-sulfur compounds can functionally provide relatively efficient (ultra-deep) removal of sulfur. Non-limiting examples of organo-sulfur compounds that can advantageously be removed from said hydrocarbon stream can include, but are not limited to, mercaptans, sulfides, disulfides, thiophenes, hydrocarbyl-substituted thiophenes, benzothiophenes, hydrocarbyl-substituted benzothiophenes, dibenzothiophenes, hydrocarbyl-substituted dibenzothiophenes, and combinations thereof. As used herein to refer to compounds, the term "hydrocarbyl-substituted" should be understood to reference variants of said compounds containing one or more linear, branched, and/or cyclic (including bicyclic and polycyclic, as well as monocyclic) substitutional moieties that can be typically hydrocarbon in nature (e.g., alkyl, alkenyl, alkynyl, conjugated, aromatic, and/or a combination thereof) but that can additionally (or, rarely, alternately) contain one or more heteroatoms (such as oxygen, nitrogen, sulfur, and the like, and combinations thereof). Non-limiting examples of common, but not exclusive, substitutional moieties include $C_1$-$C_{24}$ alkyl, alkenyl, alkadienyl, alkapolyenyl, alkynyl, alkadiynyl, alkapolyynyl, aralkyl, alkaryl, and/or hydrocarbons with more than one of C—C double bonds, C—C triple bonds, conjugated bonds, and aromatic moieties, optionally incorporating one, two, or more oxygen, nitrogen, and/or sulfur heteroatoms therein.

Aside from the extraction of the sulfur-containing compounds, as a result of the adsorptive desulfurization methods according to the invention, no other changes in the composition of hydrocarbon (diesel fuel) stream were detectable between feed and product effluent. Additionally or alternately, the adsorptive desulfurization methods according to the invention can exhibit a selectivity for adsorbing heteroatom- (particularly sulfur-) containing hydrocarbon compounds (such as described herein) in the hydrocarbon feed over non-heteroatom-(particularly non-sulfur-) containing hydrocarbon compounds (such as un-heteroatom-substituted alkenes, alkadienes, alkapolyenes, alkynes, alkadiynes, alkapolyynes, alkanes, aromatics, aralkyl species, alkaryl species, and combinations thereof; additionally or alternately, where a specific heteroatom selectivity is sought, such as for sulfur, the aforementioned selectivity can compare the sulfur-containing hydrocarbons to the non-sulfur-containing hydrocarbons, including nitrogen- and/or oxygen-containing hydrocarbons, for example, as well as the other non-heteroatom-containing hydrocarbons such as enumerated herein, and/or can compare the sulfur-containing hydrocarbons only to the non-heteroatom-containing hydrocarbons such as enumerated herein) of at least 3:1, e.g., at least 4:1, at least 5:1, at least 7.5:1, at least 10:1, at least 15:1, at least 20:1, at least 25:1, or at least 50:1.

ADDITIONAL EMBODIMENTS

Additionally or alternately, the present invention can include one or more of the following embodiments.

Embodiment 1

An adsorbent composition for removing sulfur moieties from a hydrocarbon feed, the composition comprising: a nanocrystal complex comprised of approximately 2-10 nm sized crystals of elemental Ni having associated therewith a plurality of chemical moieties selected from the group consisting of elemental phosphorus, phosphine moieties ($PH_x$), and combinations thereof, wherein said nanocrystal complex exhibits a molar ratio of P to Ni from about 0.2 to about 0.6, and wherein said nanocrystal complex is supported on a refractory support material.

Embodiment 2

The adsorbent composition of embodiment 1, wherein: said Ni particles comprise from 30 wt % to 50 wt % of the active phases of the adsorbent; said Ni particles comprise greater than 25 wt % of the adsorbent composition; the Ni particles comprise from 35 wt % to 45 wt % of the adsorbent composition; or a combination thereof.

Embodiment 3

The adsorbent composition of embodiment 1 or embodiment 2, wherein said refractory support: is selected from the group consisting of micro-mesoporous silica, mesoporous silica, meso-structured silica, silica-alumina, carbon, and mixtures thereof; has a surface area ranging from about 150 m$^2$/g to about 1000 m$^2$/g; has an average pore diameter from 3 nm to 30 nm; or a combination thereof.

Embodiment 4

A sulfur-adsorbed composition comprising the adsorbent composition of any one of the previous embodiments, to which at least about 1.8 grams (or at least about 2 grams) of sulfur compounds per 100 grams of adsorbent composition are adsorbed.

Embodiment 5

A process for making an adsorbent for removing sulfur from a hydrocarbon stream, said process comprising: (a) providing a support selected from the group consisting of micro-mesoporous silica, mesoporous silica, meso-structured silica, alumina, and mixtures and combinations thereof; (b) depositing on said support a combination of nickel oxide and one or more $Ni_y$—$P_z$—$O_n$ complexes, wherein y is from 1 to 3, z is from 2 to 4, and n is from 7 to 12, and wherein the combination of nickel oxide and one or more $Ni_y$—$P_z$—$O_n$ complexes have a first average particle size; and (c) reducing said combination of nickel oxide and $Ni_y$—$P_z$—$O_n$ complexes, thereby resulting in a plurality of Ni nanoparticles having a second average particle size and with which is (are) associated one or more chemical species selected from the group consisting of elemental phosphorus, phosphine ($PH_x$) species, and combinations thereof, wherein: (i) the second average particle size is smaller than the first average particle size by up to 80%, by at least 15%, or both; (ii) the first average particle size is in the range from about 4 nm to about 10 nm and the second average particle size is in the range from about 2 nm to about 6 nm; or (iii) both (i) and (ii).

Embodiment 6

The method of embodiment 5, wherein the refractory support: is selected from the group consisting of mesoporous silica, mesoporous alumina, mesoporous silica-alumina, or a combination thereof; has a surface area from about 150 m$^2$/g to 1000 m$^2$/g and an average pore size from 3 nm to 30 nm; or a combination thereof.

Embodiment 7

The method of embodiment 5 or embodiment 6, wherein the combination of nickel oxide and $Ni_y$—$P_z$—$O_n$ complex(es) is deposited on said support so as to achieve an atomic ratio of Ni/P from 4.5 to 8.5 and a nickel content from 15 wt % to 50 wt %, based on the weight of the adsorbent composition.

Embodiment 8

A method for adsorptive removal of sulfur from a hydrocarbon stream comprising: (i) contacting said hydrocarbon stream with the adsorbent composition of any one of embodiments 1-3 under conditions sufficient to achieve a single-pass adsorption capacity for sulfur compounds of more than 1.6 grams of sulfur compounds per 100 grams of adsorbent composition, wherein the refractory support comprises silica, silica-alumina, carbon, or a combination thereof; (ii) contacting said hydrocarbon stream with an adsorbent composition comprising a nanocrystal complex including nanocrystals of elemental Ni having associated therewith a plurality of chemical moieties selected from the group consisting of elemental phosphorus, phosphine moieties ($PH_x$), and combinations thereof, wherein said nanocrystal complex exhibits a molar ratio of P to Ni from about 0.2 to about 0.6, and wherein said nanocrystal complex is supported on a refractory support material comprising silica, silica-alumina, carbon, or a combination thereof, so as to achieve the sulfur-adsorbed composition of embodiment 4; or (iii) contacting said hydrocarbon stream with an adsorbent composition made according to the method of any one of embodiments 5-7, wherein the refractory support comprises silica, silica-alumina, carbon, or a combination thereof.

Embodiment 9

The method of embodiment 8, wherein sulfur removal is accomplished without added hydrogen.

Embodiment 10

The method of embodiment 8 or embodiment 9, wherein organo-sulfur compounds are removed from said hydrocarbon stream, said organo-sulfur compounds comprising mercaptans, sulfides, disulfides, thiophenes, hydrocarbyl-substituted thiophenes, benzothiophenes, hydrocarbyl-substituted benzothiophenes, dibenzothiophenes, hydrocarbyl-substituted dibenzothiophenes, or combinations thereof.

Embodiment 11

The method of any one of embodiments 8-10, wherein the contacting occurs: at an LHSV from about 5 hr$^{-1}$ to about 40 hr$^{-1}$; at a temperature between about 250° C. and about 400° C. (e.g., from about 275° C. to about 360° C.); or a combination thereof.

Embodiment 12

The method of any one of embodiments 8-11, wherein the adsorptive desulfurization exhibits a selectivity for sulfur-containing hydrocarbon compounds over non-sulfur-containing hydrocarbon compounds of at least 3:1.

The invention will now be more particularly described with reference to the following non-limiting Examples and the accompanying drawings.

EXAMPLES

Example 1 (Comparative)

A sample of ~10 grams of silica gel (DAVICAT, ID-2411) having a surface area of ~400 m$^2$/g and an average pore diameter of ~8 nm was calcined at ~550° C. for ~2 hours. It was placed in a ~250 mL flask, inserted in a heating bath and provided with a magnetic stirrer and condenser, which flask also contained an aqueous solution prepared by dissolution of ~93 grams of $Ni(NO_3)_2 \cdot 6H_2O$, ~84 grams of urea, ~7 mL $HNO_3$ (70%), ~11.9 grams of $(NH_4)_2HPO_4$, and ~150 mL of $H_2O$. The mixture was heated to ~80° C. and stirred at that temperature for ~24 hours. During this period, the pH increased from ~0.96 to ~5. The mixture was cooled to approximately room temperature (about 23° C.) and filtered. The resulting solid was transferred into a flask with ~200 mL distilled water at ~60° C., stirred for ~1.5 min, and filtered again. This washing procedure was repeated twice. The washed material was dried at ~120° C. for ~4 hours (heating rate ~5° C./min) and calcined in air at ~500° C. for ~6 hours (heating rate ~1° C./min). EDX analysis, performed using a Quanta 2000 Scanning Electron Microscope (SEM) commercially available from Phillips Fay Co., inter alia, indicated the contents of Ni, P, Si, and O to be ~62.8 wt %, ~13.1 wt %, ~6.4 wt %, and ~17.6 wt %, respectively. This corresponded roughly to an Ni:P atomic ratio of ~2.5. The surface area of the composite material, as measured by standard BET method, was ~175 m$^2$/g.

About 5 grams of the above composite material was reduced in a quartz reactor at approximately atmospheric pressure with a $H_2$ flux of ~1000 cm$^3$(STP)/min at ~580° C. for ~0.5 hour (heating up to ~350° C. was done at a heating rate of ~3.6° C./min, and from ~350-580° C. at ~1° C./min), then cooled in He to ambient temperature (about 20-25° C.). XRD analysis of the reduced material, referred to as BGU-5, aside from a wide (amorphous) halo centered at about 22° 2θ (believed to correspond with silica), showed 2θ peaks at ~32.7°, ~38.4°, ~41.7°, ~44.4°, ~47.0°, and ~49.0° (believed to correspond with a $Ni_{12}P_5$ phase, e.g., having a crystal domain size of ~30 nm, calculated by analyzing XRD peak widths), and at ~36.4°, ~41.8°; ~~43.6°, and ~46.6° (believed to correspond with a $Ni_3P$ phase, e.g., having a crystal domain size of ~3 nm, calculated by analyzing XRD peak widths). The total loading of these phases in the BGU-5 material was determined to be ~62.2 wt %, based on EDX and XRD phase analysis. The surface area of the reduced BGU-5 material was measured by BET techniques to be ~205 m$^2$/g.

Example 2

A sample of ~30 grams of silica gel (Grace Davison, LC-150A) having a surface area of ~320 m$^2$/g and an average pore diameter of ~15 nm was calcined at ~550° C. for ~2 hours. It was placed in a ~1 L flask, inserted in a heating mantle and provided with a mechanic stirrer and condenser, which flask also contained an aqueous solution prepared by dissolution of ~179 grams of $Ni(NO_3)_2.6H_2O$, ~202 grams of urea, ~16.8 mL $HNO_3$ (70%), ~16.0 grams of $(NH_4)_2HPO_4$, and ~300 mL of $H_2O$. The mixture was heated to ~80° C. and stirred at that temperature for ~24 hours. During this period, the pH increased from ~1.5 to ~5.5. The resulting hot mixture was filtered, and the resulting solid was transferred into a flask with ~500 mL distilled water at ~65° C., stirred for ~1.5 min, and filtered again. This washing procedure was repeated twice. The washed material was dried at ~120° C. for ~4 hours (heating rate ~5° C./min) and calcined in air at ~500° C. for ~6 hours (heating rate ~1° C./min). EDX analysis indicated the contents of Ni and P to be ~42 wt % and ~3.5 wt %, respectively. This corresponded roughly to an Ni:P atomic ratio of ~6.3.

About 1 gram of the above composite material was reduced in a quartz reactor at approximately atmospheric pressure. The temperature was raised to ~350° C. at a heating rate of ~4° C./min and then to ~580° C. at a heating rate of ~1° C./min, where it was kept at 580° C. for ~0.5 hours under a $H_2$ flow of ~500 $cm^3$(STP)/min. The reactor was then cooled to approximately room temperature (about 20-25° C.) under He. XRD analysis of the reduced material, referred to as BGU-108, aside from a wide (amorphous) halo centered at about 22° 2θ (believed to correspond with silica), showed a wide (amorphous) halo in the range of about 27-40° 2θ (believed to correspond with a portion of the $Ni_y$—$P_z$—$O_n$ complex-phosphate phase that was not reduced upon hydrogen treatment), and showed 2θ peaks at ~44.5°, ~51.8°, and ~76.4° (believed to correspond with a metallic Ni phase, e.g., having a crystal domain size of ~5 nm, calculated by analyzing XRD peak widths). The content of the Ni phase was determined to be ~27 wt %, based on XRD phase analysis. EDS analysis focused on areas comprising the Ni nanoparticles and was accomplished using a FasTEM instrument (JEOL 2010); the results showed an atomic P:Ni ratio of ~0.53 in those Ni nanoparticle areas. The surface area of the reduced BGU-108 material was measured by BET techniques to be ~230 $m^2/g$.

Example 3

A sample of ~30 grams of silica gel (Grace Davison, LC-150A) having a surface area of ~320 $m^2$/g and an average pore diameter of ~15 nm was calcined at ~550° C. for ~2 hours. It was placed in a ~1 L flask, inserted in a heating bath and provided with a mechanic stirrer and condenser, which flask also contained an aqueous solution prepared by dissolution of ~179 grams of $Ni(NO_3)_2.6H_2P$, ~202 grams of urea, ~16.8 mL $HNO_3$ (70%), ~16.0 grams of $(NH_4)_2HPO_4$, and ~300 mL of $H_2O$. The mixture was heated to ~80° C. and stirred at that temperature for ~24 hours. During this period, the pH increased from ~1.4 to ~5.6. The mixture was cooled to approximately room temperature (about 20-25° C.) and filtered. The resulting solid was transferred into a flask with ~200 mL distilled water at ~60° C., stirred for ~1.5 min, and filtered again. This washing procedure was repeated twice. The washed material was dried at ~120° C. for ~4 hours (heating rate ~5° C./min) and calcined in air at ~500° C. for ~6 hours (heating rate ~1° C./min). EDX analysis indicated the contents of Ni and P to be ~55.1 wt % and ~5.7 wt %, respectively. This corresponded roughly to an Ni:P atomic ratio of ~5.2.

About 70 grams of material prepared as described in Example 3 above was reduced in a stainless steel reactor at approximately atmospheric pressure with a $H_2$ flux of ~10 L(STP)/min at ~580° C. for ~1.5 hours (heating up to ~350° C. was done at a heating rate of ~4° C./min, and from about 350-580° C. at ~1° C./min), then cooled in hydrogen to about 450° C., and then in nitrogen to about 300° C.

At this point, a passivation procedure was exercised. Further cooling to approximately room temperature (about 20-25° C.) was conducted for ~4.5 hours with a gas mixture containing $N_2$ at ~1.5 L(STP)/min and $CO_2$ at ~90 $cm^3$(STP)/min. The flow rates of the gases were then lowered to ~0.5 L(STP)/min and ~30 $cm^3$(STP)/min, respectively, for another ~10 hours. Finally, the material was exposed to a gas mixture containing ~2 L(STP)/min of $N_2$ and ~30 $cm^3$(STP)/min of air while at room temperature for additional 2 hours.

XRD analysis of the reduced material, referred to as BGU-ZSA3, aside from a wide (amorphous) halo centered at about 22° 2θ (believed to correspond with silica), showed a wide (amorphous) halo in the range of about 27-40° 2θ (believed to correspond with a portion of the $Ni_y$—$P_z$—$O_n$ complex-phosphate phase that was not reduced upon hydrogen treatment), and showed 2θ peaks at ~44.5°, ~51.8°, and ~76.4° (believed to correspond with a metallic Ni phase, e.g., having a crystal domain size of ~4 nm, calculated by analyzing XRD peak widths). The content of the Ni phase was determined to be ~32 wt %, based on XRD phase analysis. EDS analysis focused on areas comprising the Ni nanoparticles and was accomplished using a FasTEM instrument (JEOL 2010); the results showed an atomic P:Ni ratio of ~0.22 in those Ni nanoparticle areas. The surface area of the reduced BGU-ZSA3 material was measured by BET techniques to be ~215 $m^2/g$.

Example 4

A sample of ~0.8 grams of the BGU-5 (reference) sorbent material, prepared according to Example 1 and after calcination in air, was placed into a tubular stainless steel reactor, having an internal diameter of ~5 mm and length of ~10 cm, and equipped with an internal thermowell and a heating oven. The temperature controller was used to maintain temperature within ±1° C. The adsorbent was reduced under approximately atmospheric pressure with an $H_2$ flux of ~1000 $cm^3$ (STP)/min at ~580° C. for ~0.5 hour (heating up to ~350° C. was done at a heating rate of ~3.6° C./min, and from ~350-580° C. at ~1° C./min), then cooled under hydrogen flow to the reaction temperature of ~300° C. A hydrotreated diesel fuel feed (IBP ~193° C.; FBP ~351° C.; density ~0.834 $g/cm^3$; feed composition containing ~30.6 vol % aromatic hydrocarbons; ~1.9 vol % olefins; ~67.5 vol % paraffins; and ~15 wppm sulfur) was used to test adsorbent performance. The run was started first by purging the system with helium, then using helium to increase pressure up to ~17 bar. The fuel feed was pumped at an LHSV of ~2.7 $hr^{-1}$ through the reactor, kept at ~300° C., and, after exiting the reactor, the product was collected in a cooled trap. The sulfur content in the diesel fuel at the reactor outlet ($S_{out}$, wppm) was analyzed periodically using gas chromatography (Aligent HP 6890A GC instrument equipped with chemiluminescence detector GC-335 SCD for sulfur analysis). The sorbent sulfur capacity after given a run time (t) was calculated according to the following equation:

$$S_{cap} = WHSV \int_0^{-1} \Delta C_{St}(t) dt$$

where WHSV (grams fuel/[grams sorbent*hours]) represents the weight hourly space velocity of the fuel feedstock and hours is the run time; $\Delta C_{St}(t) = (C_{Si} - C_{St})$, where $C_{Si}$ (wt %)

represents the sulfur concentration in the fuel feed, and where $C_{St}$ (wt %) represents the sulfur concentration in the treated fuel after run time t.

Figure 3:
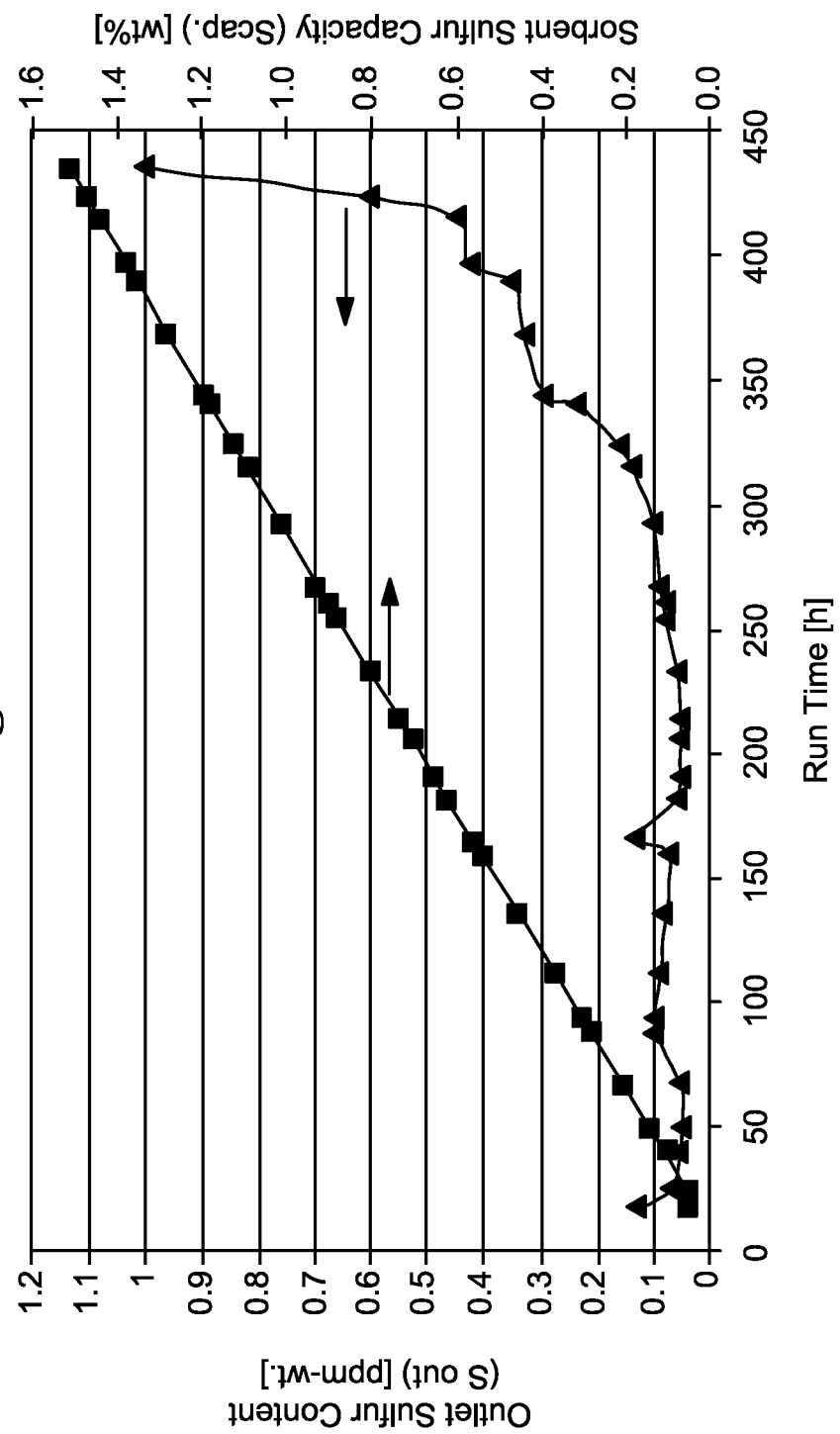
FIG. 3 graphically shows reference adsorbent performance with synthetic diesel.

The testing results of the BGU-5 reference material containing $Ni_{12}P_5$ and $Ni_3P$ phosphide phases are shown in FIG. 3, and were conducted at an LHSV of ~2.7 $hr^{-1}$. The total sulfur capacity measured for the range of sulfur in the product below ~1 wppm was about 1.5 grams of sulfur per 100 grams of adsorbent material.

Example 5

Figure 4:
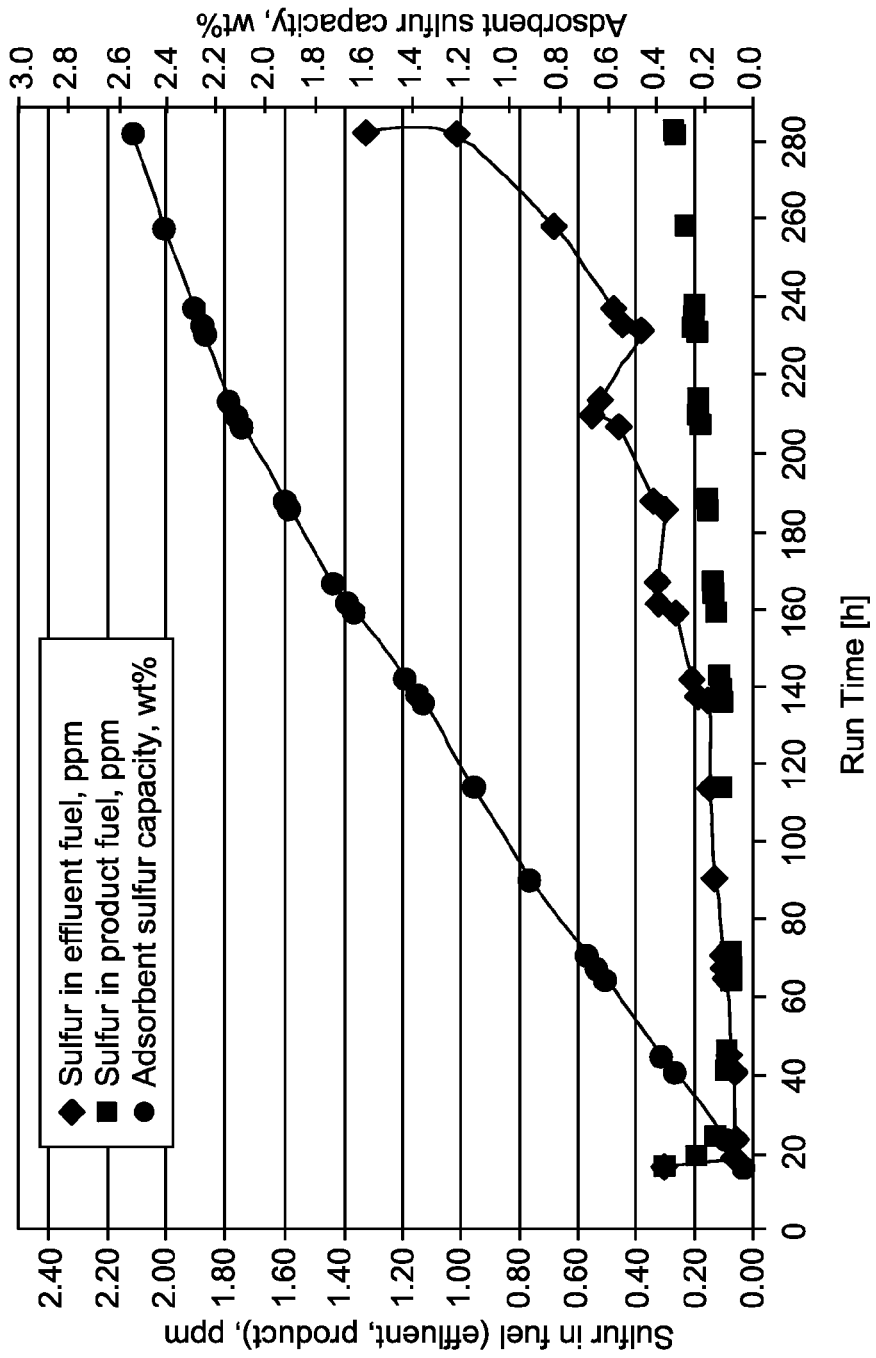
FIG. 4 graphically shows adsorbent performance with synthetic diesel.

About 1 gram of adsorbent BGU-108, prepared by the method described in Example 2, was tested in a reactor as described in Example 4. The reductive activation of the adsorbent was conducted at the conditions described in Example 2. Its performance (shown in FIG. 4) was measured by contacting with a synthetic diesel fuel feed at about 300° C. and at an LHSV of ~12 $hr^{-1}$. The sulfur capacity of the adsorbent was measured to be about 2.5 wt %, which was significantly higher than that measured in Example 4. The sulfur capacity could potentially be increased, if the cumulative average sulfur (CAS) were considered. The CAS value in this run was limited to less than ~0.4 wppm. The fact that the residence time in this case was about four times lower than that in Example 4 above is believed to indicate that the activity of the adsorbent prepared in Example 2 above was substantially higher. Therefore, the overall performance of the instantly described adsorbent(s) is believed to surpass previous results published in the art.

Example 6

Figure 5:
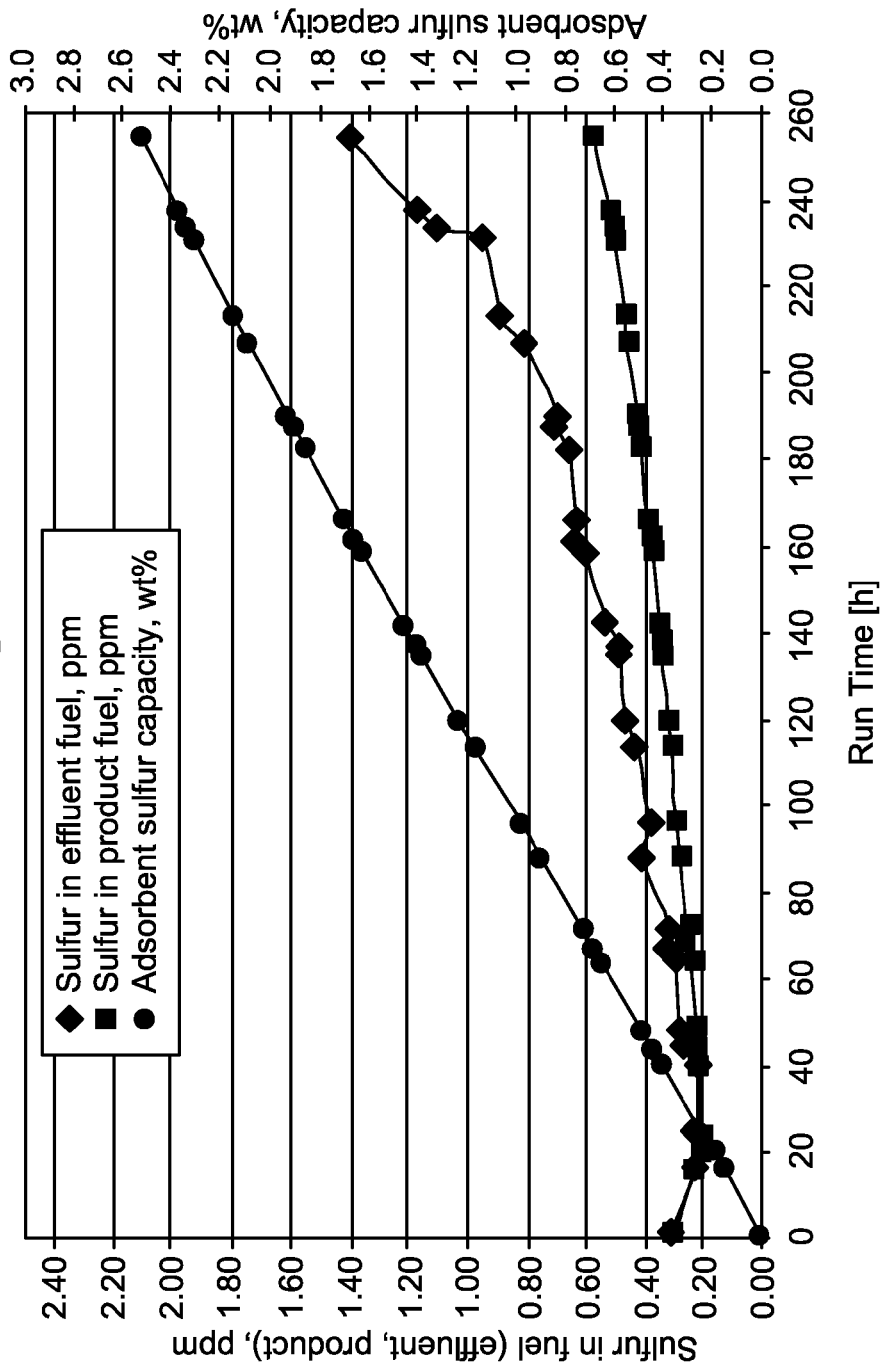
FIG. 5 graphically shows adsorbent performance with commercial diesel.

About 1 gram of adsorbent BGU-ZSA3, passivated as described in Example 3 above, was tested in a reactor described in Example 4 above. The passivated adsorbent was re-activated at ~150° C. with flowing hydrogen at ~150 $cm^3$ (STP)/min, then heated under helium flow to ~300° C. Performance of this re-activated adsorbent was measured at the operating conditions described in Example 5 above. However, the performance test involved exposure of the adsorbent to a commercial diesel containing ~10 wppm sulfur. The results (shown in FIG. 5) indicated that the sulfur capacity decreased only mildly to about 2.3 wt %, despite the fact that the commercial diesel contained additives that would have been expected to implicate a more significant sulfur capacity decrease.

Example 7

Figure 6:
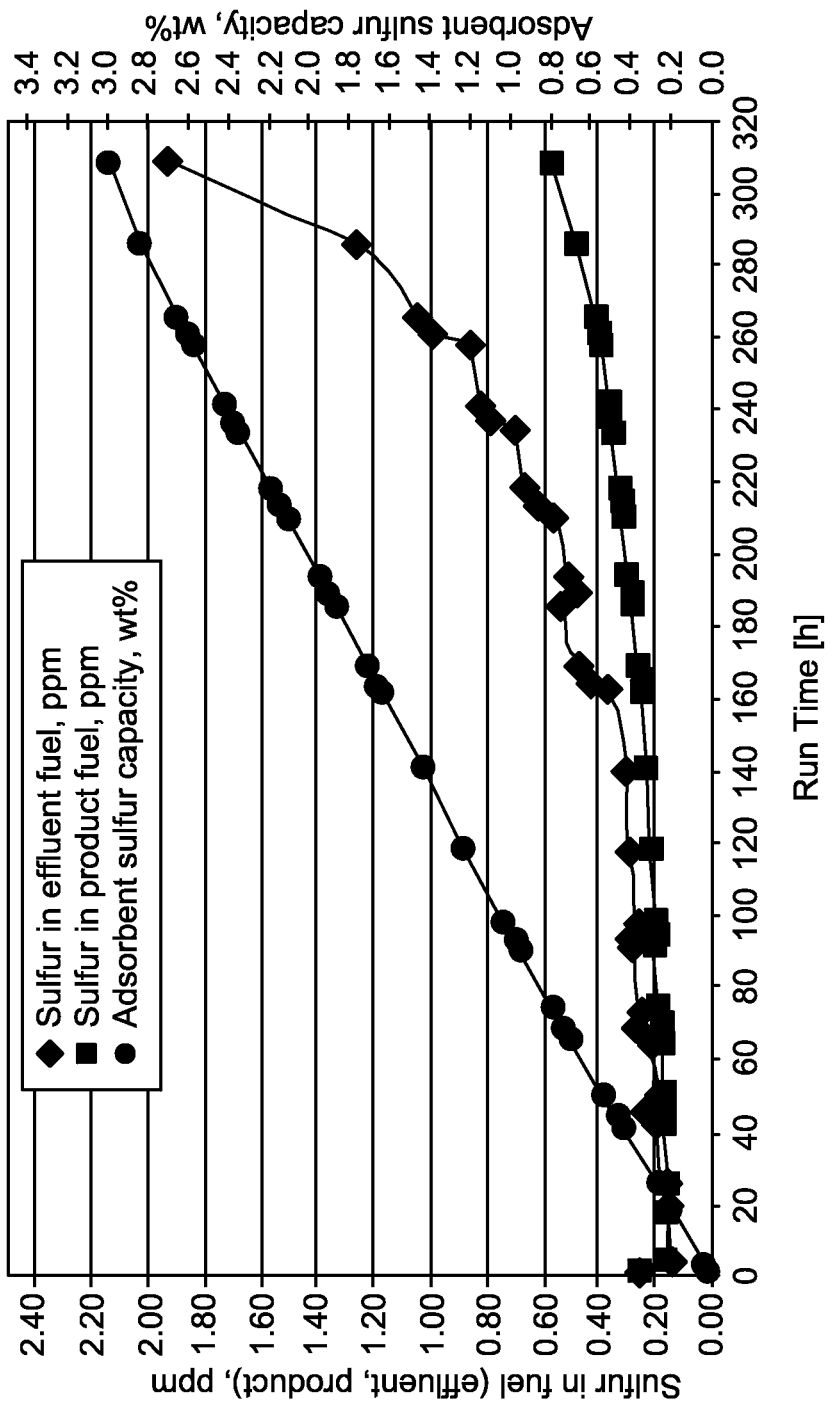
FIG. 6 graphically shows adsorbent performance with commercial diesel at a higher temperatures.

About 1 gram of adsorbent BGU-ZSA3, passivated as described in Example 3 above, was tested in a reactor described in Example 4 above. The passivated adsorbent was re-activated at ~150° C. with flowing hydrogen at ~150 $cm^3$ (STP)/min, then heated under helium flow to ~330° C. Aside from the higher temperature, all other operating conditions were the same as described in Example 6 above. The results (shown in FIG. 6) indicated that the sulfur capacity of the adsorbent increased to about 2.6 wt %, with sulfur content in the effluent diesel below ~1 wppm. It should be noted that the cumulative average sulfur content in the resulting product was still below ~1 wppm at an adsorbent sulfur capacity of ~3 wt %. Therefore, as the temperature increased significantly, so did the sulfur capacity and, as expected, the rate of sulfur removal.

Example 8

Figure 7:
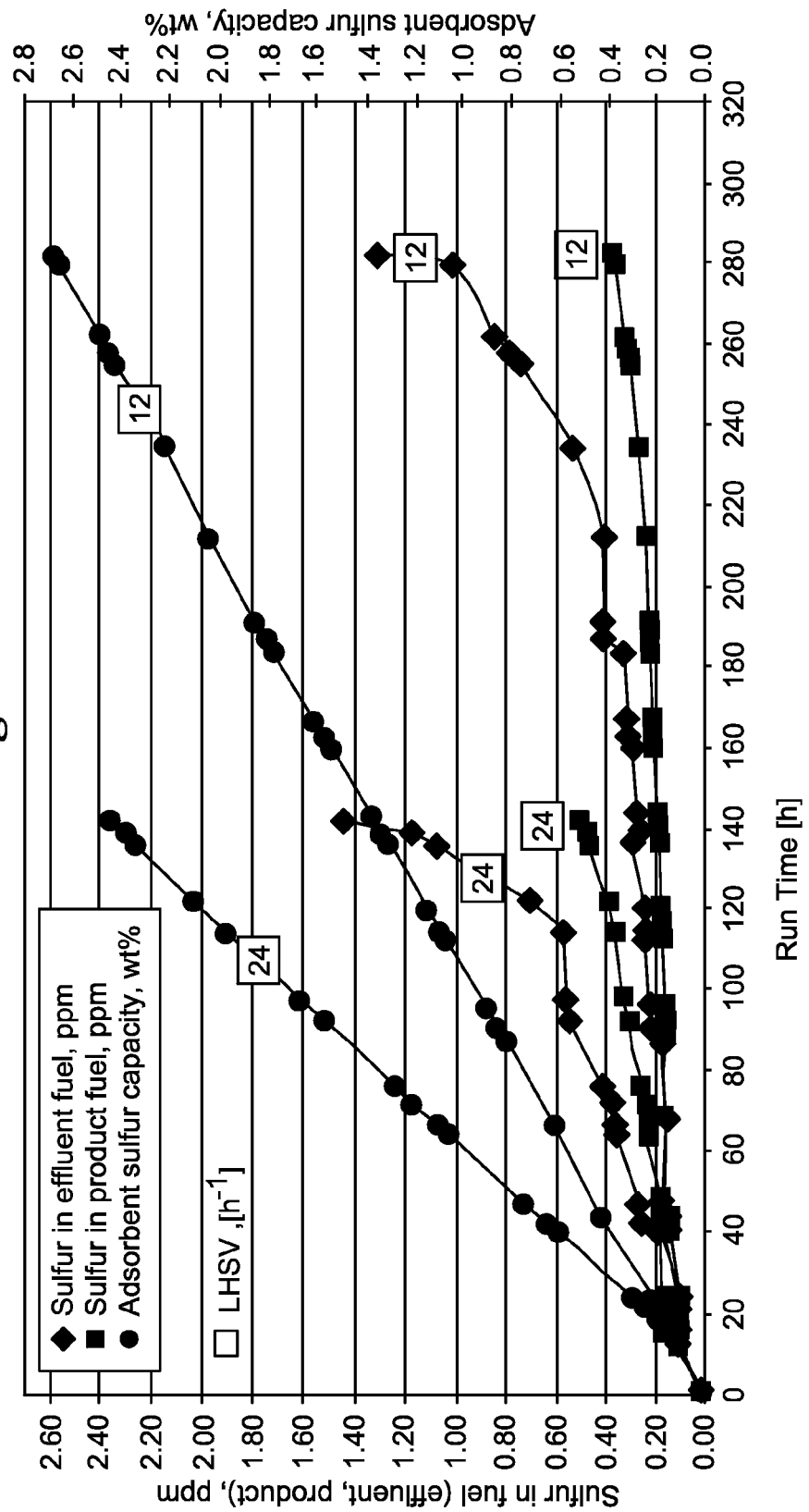
FIG. 7 graphically shows adsorbent performance with commercial diesel at various LHSVs.

About 1 gram of adsorbent BGU-108, prepared by the method described in Example 2, was tested in a reactor described in Example 4. The activation of the adsorbent was conducted at the conditions described in Example 2. Its performance (shown in FIG. 7) was measured by contacting with a commercial diesel fuel feed at about 330° C. across two LHSV values (~12 $hr^{-1}$ and ~24 $hr^{-1}$). The results clearly indicated that the activity of this adsorbent was surprisingly high. The product sulfur content was relatively low at the LHSV of ~24 $hr^{-1}$. The sulfur capacity was about the same at the two LHSV values tested.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A method for adsorptive removal of sulfur from a hydrocarbon stream, the method comprising contacting said hydrocarbon stream with an adsorbent composition under conditions sufficient to achieve a single-pass adsorption capacity for sulfur compounds of more than 1.6 grams of sulfur compounds per 100 grams of the adsorbent composition, the adsorbent composition comprising: a nanocrystal complex comprised of approximately 2-10 nm sized crystals of elemental Ni having associated therewith a plurality of chemical moieties selected from the group consisting of elemental phosphorus, phosphine moieties ($PH_x$), and combinations thereof, wherein said nanocrystal complex exhibits a molar ratio of P to Ni from about 0.2 to about 0.6, and a refractory support material comprising micro-mesoporous silica, mesoporous silica, meso-structured silica, alumina, and mixtures and combinations thereof;

said adsorbent composition made by a process comprising:
a) providing the refractory support material;
b) depositing on said support material a combination of nickel oxide and one or more $Ni_y$—$P_z$—$O_n$ complexes, wherein y is from 1 to 3, z is from 2 to 4, and n is from 7 to 12, and wherein the combination of nickel oxide and one or more $Ni_y$—$P_z$—$O_n$ complexes have a first average particle size; and
c) reducing said combination of nickel oxide and $Ni_y$—$P_z$—$O_n$ complexes, thereby resulting in a plurality of Ni nanoparticles having a second average particle size having associated therewith one or more chemical species selected from the group consisting of elemental phosphorus, phosphine ($PH_x$) species, and combinations thereof,
wherein: (i) the second average particle size is smaller than the first average particle size by up to 80%, by at least 15%, or both; (ii) the first average particle size is in the range from about 4 nm to about 10 nm and the second average particle size is in the range from about 2 nm to about 6 nm; or (iii) both (i) and (ii).

2. The method of claim 1, wherein said Ni nanoparticles comprise from 30 wt % to 50 wt % of active phases of the adsorbent composition.

3. The method of claim 2, wherein said Ni nanoparticles comprise greater than 25 wt % of the adsorbent composition.

4. The method of claim 3, wherein the Ni particles comprise from about 35 wt % to about 45 wt % of the adsorbent composition.

5. The method of claim 1, wherein said refractory support material is further characterized as having a surface area ranging from about 150 $m^2/g$ to about 1000 $m^2/g$.

6. The method of claim 5, wherein the said refractory support material is further characterized as having an average pore diameter from about 3 nm to about 30 nm.

7. The method of claim 1, wherein the combination of nickel oxide and $Ni_y$—$P_z$—$O_n$ complex(es) is deposited on said support so as to achieve an atomic ratio of Ni/P from about 4.5 to about 8.5 and a nickel content from about 15 wt % to about 50 wt %, based on the weight of the adsorbent composition.

8. The method of claim 1, wherein sulfur removal is accomplished without added hydrogen.

9. The method of claim 1, wherein said sulfur compounds are selected from the group consisting of mercaptans, sulfides, disulfides, thiophenes, hydrocarbyl-substituted thiophenes, benzothiophenes, hydrocarbyl-substituted benzothiophenes, dibenzothiophenes, hydrocarbyl-substituted dibenzothiophenes, and combinations thereof.

10. The method of claim 1, wherein the contacting occurs at an LHSV from about 5 $hr^{-1}$ to about 40 $hr^{-1}$.

11. The method of claim 1, wherein the contacting occurs at a temperature between about 250° C. and about 400° C.

12. The method of claim 1 having a selectivity for sulfur-containing hydrocarbon compounds over non-sulfur-containing hydrocarbon compounds of at least 3:1.

\* \* \* \* \*